United States Patent
Eitouni

(10) Patent No.: US 8,404,873 B2
(45) Date of Patent: Mar. 26, 2013

(54) AMBIENT TEMPERATURE PURIFICATION OF ALKYLENE OXIDES

(75) Inventor: Hany Basam Eitouni, Oakland, CA (US)

(73) Assignee: Seeo, Inc, Hayward, CA (US)

( * ) Notice: Subject to any disclaimer, the term of this patent is extended or adjusted under 35 U.S.C. 154(b) by 348 days.

(21) Appl. No.: 12/757,933

(22) Filed: Apr. 9, 2010

(65) Prior Publication Data

US 2011/0190519 A1 Aug. 4, 2011

Related U.S. Application Data

(60) Provisional application No. 61/300,744, filed on Feb. 2, 2010.

(51) Int. Cl.
*C07D 301/32* (2006.01)

(52) U.S. Cl. .......................... 549/541; 549/542

(58) Field of Classification Search .................. 549/541, 549/542
See application file for complete search history.

(56) References Cited

U.S. PATENT DOCUMENTS

| | | |
|---|---|---|
| 3,578,568 A | 5/1971 | Washall |
| 3,745,092 A | 7/1973 | Vanderwater |
| 3,987,065 A | 10/1976 | Dennis |
| 4,033,617 A | 7/1977 | Cocuzza |
| 4,778,567 A | 10/1988 | Kakimoto |
| 5,006,206 A | 4/1991 | Shih |
| 5,107,022 A | 4/1992 | de Besset |
| 5,340,446 A | 8/1994 | Nelson |
| 5,489,366 A * | 2/1996 | Jongenburger ................. 203/14 |
| 7,541,417 B2 | 6/2009 | Ashtekar et al. |

OTHER PUBLICATIONS

Kanehiro Nakamura, Ryuichi Endo, and Masatami Takeda "Solution Behavior of Styrene-Ethylene Oxide Block Copolymers," Journal of Polymer Science, Polymer Physics Edition vol. 14, 135-142 (1976).
Nikos Hadjichristidis, Herm Iatrou, Stergios Pispas, Marinos Pitsikalis, "Anionic Polymerization: High Vacuum Techniques," Journal of Polymer Science: Part A: Polymer Chemistry, vol. 38, 3211-3234 (2000).

* cited by examiner

*Primary Examiner* — Taylor Victor Oh
(74) *Attorney, Agent, or Firm* — R'Sue Popowich Caron

(57) ABSTRACT

A new purification technique for alkylene oxides is described. The technique is safer than previously reported methods and does not require cooling of the purification vessel. In a solution of a high-boiling point solvent and butyllithium, an alkylene oxide is added and allowed to react at ambient temperature. The impurities readily react with the butyllithium while the alkylene oxide does not. The low-boiling alkylene oxide is then easily distilled out of the high-boiling point solvent as a pure material ready for use in controlled polymerization reactions.

22 Claims, 1 Drawing Sheet

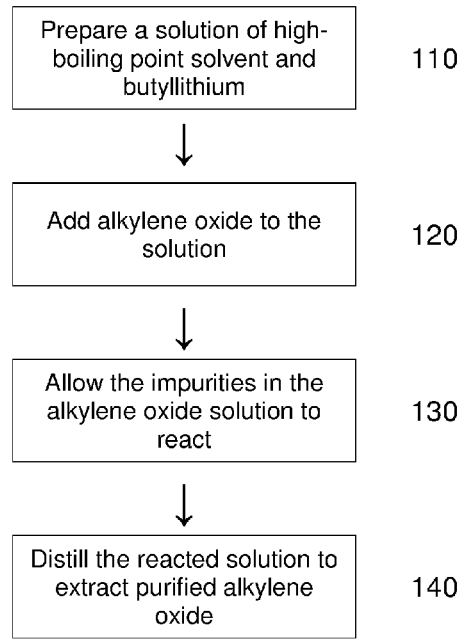

```
┌─────────────────────────┐
│  Prepare a solution of high-│
│  boiling point solvent and  │    110
│       butyllithium          │
└─────────────────────────┘
              │
              ▼
┌─────────────────────────┐
│  Add alkylene oxide to the  │    120
│         solution            │
└─────────────────────────┘
              │
              ▼
┌─────────────────────────┐
│  Allow the impurities in the│
│  alkylene oxide solution to │    130
│           react             │
└─────────────────────────┘
              │
              ▼
┌─────────────────────────┐
│ Distill the reacted solution to│
│  extract purified alkylene  │    140
│           oxide             │
└─────────────────────────┘
```

AMBIENT TEMPERATURE PURIFICATION OF ALKYLENE OXIDES

CROSS-REFERENCE TO RELATED APPLICATIONS

This application claims priority to U.S. Provisional Patent Application 61/300,744, filed Feb. 2, 2010, which is incorporated by reference herein.

BACKGROUND OF THE INVENTION

Field of the Invention

This invention relates generally to a method of purifying organic materials and, more specifically, to a safe, non-explosive method of purifying alkylene oxide materials.

Extremely pure monomers are needed for anionic polymerization and even more so for block copolymers. Yet alkylene oxides are notoriously difficult to purify. When making homopolymers or low molecular weight block copolymers, alkylene oxides can be purified by stirring on relatively mild drying agents such as calcium hydride. However, for block copolymers, and especially for high molecular weight block copolymers, more aggressive drying agents are used. Often monomer purification is performed using drying agents that are reactive and can often initiate polymerization themselves. These methods are extremely dangerous, and the temperature of the system must be well controlled. Temperatures must be kept below the boiling point of the monomer and also below the temperature at which rapid polymerization occurs. If rapid polymerization occurs, the exotherm from the polymerization heats the system, resulting in a runaway reaction and possible explosion. Cooling the purification reaction to below ambient temperatures is costly and presents an extreme safety risk in the event of cooling failure. The methods described herein present a new purification strategy for safe and effective alkylene oxide purification at ambient temperatures.

BRIEF DESCRIPTION OF THE DRAWINGS

FIG. 1 is a flow chart that shows steps for purifying alkylene oxide, according to an embodiment of the invention.

DETAILED DESCRIPTION

The aforementioned needs are satisfied by the process of the present invention which comprises a new and very safe method of purify alkylene oxides. The unprecedented safety of the procedure and other objects and advantages of the present invention will become more fully apparent from the following description.

All publications referred to herein are incorporated by reference in their entirety for all purposes as if fully set forth herein.

Alkylene oxides are routinely purified by fractional distillation. Further purification can be achieved by using an aqueous absorber/stripper system, but the purified alkylene oxide may still contain impurities such as water, aldehydes, and carbon dioxide. The crude alkylene oxide material may be passed through a dehydrator followed by separation steps to remove light and heavy impurities. However, such methods result in a material that still contains traces of moisture and other small molecules that can have a detrimental effect on any subsequent anionic polymerization. Details of current methods can be found in U.S. Pat. Nos. 4,033,617 and 4,778,567. Drying agents such as calcium hydride have been employed to remove remaining water, but they cannot remove trace amounts of carbon dioxide and aldehydes. To remove such impurities, a more aggressive technique is used, which involves reactive metals such as potassium (Nakamura, K.; Endo, R.; Takeda, M., *J Polym Sci Polym Phys Ed* 1976, 14, 135-142.). However, this procedure can produce polymerization initiators that lead to a dangerous runaway polymerization reaction. To avoid this possibility, alkyl lithium drying agents such as n-butyllithium can be used in place of reactive metal, as described in U.S. Pat. No. 3,987,065 and in Hadjichrisitidis, N.; Iatrou, H.; Pispas, S.; Pitsikalis M., *J Polym Sci Part A: Polym Chem* 2000, 38, 3211-3234. However, in this method the purification unit must be kept between −50° C. and 0° C., which adds considerable cost to the procedure. More importantly, the procedure can become dangerous if the mixture is allowed to warm above 0° C., where uncontrolled polymerization can again lead to an explosion.

When diluted in high-boiling point solvents, alkylene oxides do not polymerize readily in the presence of purifying agents such as alkyllitihium initiators. If polymerization occurs at all, it is very slow. The opposite occurs for alkylene oxide monomers in the absence of a high-boiling point, solvent (in bulk), where purifying agents such as alkyllithium reagents not only purify the monomers but can cause dangerously rapid polymerization. In a surprising discovery, the significant difference in reactivity can be exploited to develop a safe purification strategy for alkylene oxides. In one embodiment of the invention, at ambient temperature, in a solution of a high-boiling point solvent and a purifying agent, alkylene oxide is added and allowed to react. The impurities in the alkylene oxide react readily with the purifying agent, while the alkylene oxide either polymerizes very slowly or does not polymerize at all. In one arrangement, the purifying agent can be any one or more of $CaH_2$, $BaO$, organolithiums, alkylmagnesiums, alkylaluminums, alkali metals, alkaline earth metals, zeolites, molecular sieves, or other common drying agents. In one arrangement, the purifying agent can butyllithium (e.g., n-butyllithium). The low-boiling alkylene oxide monomer is then easily distilled out of the high-boiling point solvent as a pure material ready for use in controlled polymerization reactions. This technique has the advantages that: 1) it is safer than purifying in bulk on an alkyllithium and 2) due to its slow reaction kinetics, it does not require cooling. Thus the purification of alkylene oxides can be performed safely at ambient temperatures by stiffing on butyllithium in a solvent.

In one embodiment of the invention, there is no restriction on the temperature at which the reaction of the alkylene oxide in the solution of high-boiling point solvent and butyllithium occurs. The reaction occurs easily at ambient temperature; no additional cooling is required. If desired, the solution may be cooled below ambient temperature, but it will slow the purification reaction. The solution may be heated above ambient temperature to speed up the purification reaction.

It should be understood that highest monomer purification efficiencies can be achieved when no polymerization of the monomer occurs during the process. The amount of monomer that polymerizes during the purification process accounts for that much less process yield of purified monomer. Therefore, a purification temperature at which little or no polymerization occurs offers greater yields than a purification temperature at which some or much polymerization occurs. In one embodiment of the invention, the term "little polymerization" is used to mean less than 50% polymerization. In one embodiment of the invention, the term "little polymerization" is used to mean less than 40% polymerization. In one embodiment of the invention, the term "little polymerization" is used to mean less than 30% polymerization. In one embodiment of the invention, the term "little polymerization" is used to mean less than 20% polymerization. In one embodiment of the invention, the term "little polymerization" is used to mean less than 10% polymerization.

In industrial processes, tradeoffs are often made. In using the methods disclosed herein, sometimes it may be advantageous to use a purification temperature where, for example, 50% or more of the monomer polymerizes, resulting in less than 50% purified monomer yield. This is essentially a question of economics: if using such a temperature causes the process to be performed less expensively, then it may be worth it to accept such low yields.

In other circumstances, purified polymer may be desired. Then, it may be desirable to use a purification temperature at which polymerization occurs.

In one embodiment of the invention, there is no restriction on the temperature of purification except that the temperature is below the boiling point of the solvent.

The steps of the method, according to an embodiment of the invention, are shown in FIG. 1. In step 110, a solution of high-boiling point solvent and butyllithium is prepared. In step 120, alkylene oxide is added to the solution. In step 130, the impurities in the alkylene oxide solution react. In step 140, the reacted solution is distilled in order to extract purified alkylene oxide.

In one embodiment of the invention, the alkylene oxide can be chosen from, but is not limited to, any one or more of ethylene oxide, propylene oxide, epoxy butane, and other substituted oxiranes.

In one embodiment of the invention the high-boiling point solvent may or may not be polar and can be chosen from, but is not limited to, toluene, xylenes, hexane, heptanes, higher alkanes, ethylbenzene, cyclohexane, and substituted aromatic compounds. In another arrangement, any solvent that has a boiling point higher than the boiling point of the alkylene oxide can be used. In one arrangement, any solvent that has a boiling point higher than 65° C. can be used.

In another embodiment of the invention the method of purification can be used on materials other than alkylene oxides and with purifying agents other than alkyllithiums. Other possibilities include any monomer that does not polymerize rapidly in high-boiling point solvents and monomers that polymerize only at temperatures below the purification temperature. One such example is alpha methylstyrene which can be purified above its polymerization ceiling temperature (61° C.). Other examples (and their ceiling temperatures) include, but are not limited to, isobutylene (50° C.), acetaldehyde (−31° C.), tetrahydrofuran (80° C.), and thioacetone (95° C.). As discussed above in regard to purification temperature, the discussion about choice of monomer and purifying agent has to do with those that maximize purified monomer yield. If high yields are not very important or if they can be sacrificed in a tradeoff for other desirable aspects of the process, yet other monomers and purifying agents, even those that may result in substantial polymerization, can be used.

In one embodiment of the invention, high-boiling point, nonpolar solvents are used to dissolve the material to be purified. In some arrangements, nonpolar solvents help to retard polymerization. For example, it can be useful to use high-boiling point, nonpolar solvents in the purification of alkylene oxides. In another embodiment of the invention, if the material to be purified undergoes no more than minimal polymerization in the presence of a polar solvent, then a high-boiling point, polar solvent can be used to dissolve the material. For example, a high-boiling point, polar solvent can be used in the purification of butadiene on $CaH_2$. As discussed above in regard to purification temperature, the discussion about choice of solvent polarity has to do with ways to maximize purified monomer yield. If high yields are not very important or if they can be sacrificed in a tradeoff for other desirable aspects of the process, solvents that may promote polymerization can be used.

In yet another embodiment of the invention, the process described herein can be scaled up to purify large volumes of alkylene oxides or other monomers as described above. It is useful to prepare the solution of high-boiling point solvent and butyllithium in a reactor, such as a stainless steel reactor. The solution is sparged with dry nitrogen to remove air that may be trapped in the solution. Alkylene oxide or any desired monomer is charged into the reactor via a condenser and diptube. It is useful to position the diptube near the bottom of the reactor so that the monomer can have maximum residence time in the solution. The solution is stirred vigorously at a temperature between about 25° C. and 110° C. As the continuously-added monomer bubbles through the solution, the purified result is removed from the reactor by means of a condenser. Then the purified monomer can be condensed into a polymerization reactor.

EXAMPLES

The following examples provide details relating to composition, fabrication and performance characteristics of block copolymer electrolytes in accordance with the present invention. It should be understood the following is representative only, and that the invention is not limited by the detail set forth in these examples.

Example 1

One liter of toluene is charged into a 2 L flask. To the toluene flask, 5 mL of a 1.6M solution of n-butyllithium in hexanes is added. The solution is degassed to remove air by freeze-pump-thaw methods and is then stirred using a magnetic stirring bar. Ethylene oxide (180 g) is then distilled by vacuum transfer into the n-butyllithium/toluene solution and stirred at room temperature to allow the impurities to react with the n-butyllithium. The purified ethylene oxide is then removed by vacuum distillation and condensed either in a receiving flask or directly into a polymerization reactor.

Example 2

One liter of xylene is charged into a 2 L flask. To the xylene flask, 5 mL of a 1.6M solution of n-butyllithium in hexanes is added. The solution is sparged with dry nitrogen to remove air and is stirred using a mechanical stirring rod. Propylene oxide (170 g) is then charged into the flask. The solution is stirred at room temperature to complete the purification. The propylene oxide is then distilled out of the purification solution by heating the flask and is condensed in a receiving flask or polymerization reactor.

Example 3

Ten liters of xylene is charged into a 20 L stainless steel reactor. To the xylene containing reactor, 50 mL of a 1.6M solution of n-butyllithium in hexanes is added. The solution is sparged with dry nitrogen to remove air and is stirred using a mechanical stirring rod. Ethylene oxide (1.8 kg) is charged into the reactor via a condenser and diptube. The diptube is positioned near the bottom of the reactor to allow maximum residence time in the solution. The solution is vigorously stirred at 55° C. The ethylene oxide bubbles through the purification solution and is continuously removed from the reactor by means of a condenser. The purified ethylene oxide is condensed into a polymerization reactor.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

I claim:

1. A method for purifying monomers, comprising the steps of:
    a) preparing a first solution of a high-boiling point nonpolar solvent and a purifying agent;
    b) dissolving a monomer in the first solution to form a second solution while holding the second solution at a purification temperature;
    c) allowing the second solution to react at the purification temperature; and
    d) distilling the pure monomer out of the second solution.

2. The method of claim 1 wherein the high-boiling point solvent is selected from the group consisting of toluene, xylenes, hexane, heptanes, higher alkanes, ethylbenzene, and cyclohexane.

3. The method of claim 1 wherein the high-boiling point solvent has a boiling temperature higher than both the boiling point of the monomer and the purification temperature.

4. The method of claim 1 wherein the purifying agent is selected from the group consisting of $CaH_2$, BaO, organolithiums, alkylmagnesiums, alkylaluminums, alkali metals, alkaline earth metals, zeolites, molecular sieves.

5. The method of claim 1 wherein the purifying agent has one or more organolithiums.

6. The method of claim 1 wherein the monomer has alpha methylstyrene.

7. The method of claim 1 wherein the monomer has alkylene oxide.

8. The method of claim 7 wherein the alkylene oxide is selected from the group consisting of ethylene oxide, propylene oxide, and epoxy butane.

9. The method of claim 1 wherein the monomer undergoes little or no polymerization in the second solution at the purification temperature.

10. The method of claim 1 wherein the purification temperature is no less than 25° C.

11. A method for purifying alkylene oxides, comprising the steps of:
    a) preparing a first solution of a high-boiling point nonpolar solvent and an organolithium;
    b) dissolving an alkylene oxide in the first solution to form a second solution while holding the second solution at a purification temperature;
    c) allowing the second solution to react at the purification temperature; and
    d) distilling the pure alkylene oxide out of the second solution.

12. The method of claim 11 wherein the high-boiling point solvent is selected from the group consisting of toluene, xylenes, hexane, heptanes, higher alkanes, ethylbenzene, and cyclohexane.

13. The method of claim 11 wherein the organolithium has butyllithium.

14. The method of claim 11 wherein the alkylene oxide is selected from the group consisting of ethylene oxide, propylene oxide, and epoxy butane.

15. The method of claim 11 wherein the high-boiling solvent has a boiling temperature higher than both the boiling temperature of the alkylene oxide and the purification temperature.

16. The method of claim 11 wherein the alkylene oxide undergoes little or no polymerization in the second solution at the purification temperature.

17. The method of claim 11 wherein the purification temperature is ambient temperature.

18. The method of claim 11 wherein step a) further comprises:
    positioning the first solution in a reactor; and
    sparging the first solution with dry nitrogen.

19. The method of claim 18 wherein step b) comprises adding the alkylene oxide to the first solution by charging via a condenser and diptube, wherein the diptube is positioned near the bottom of the reactor.

20. The method of claim 19 wherein step c) comprises stirring the second solution vigorously between about 25° C. and 110° C.

21. The method of claim 20 wherein step d) comprises removing the purified alkylene oxide from the reactor continuously by means of a condenser as crude alkylene oxide is added to the second solution continuously.

22. A method for purifying monomers, comprising the steps of:
    a) preparing a first solution of a high-boiling point nonpolar solvent and an organo lithium;
    b) dissolving a monomer in the first solution to form a second solution, while holding the second solution at a purification temperature;
    c) allowing the second solution to react at the purification temperature; and
    d) distilling the pure monomer out of the second solution.

* * * * *